(12) United States Patent
Shen et al.

(10) Patent No.: US 7,201,173 B2
(45) Date of Patent: Apr. 10, 2007

(54) DENTAL FLOSS HOLDER

(76) Inventors: Chung-Shan Shen, 58, Ma Yuan West St., Taichung (TW); Chi-Ching Shen, 58, Ma Yuan West St., Taichung (TW)

(*) Notice: Subject to any disclaimer, the term of this patent is extended or adjusted under 35 U.S.C. 154(b) by 418 days.

(21) Appl. No.: 10/840,045

(22) Filed: May 7, 2004

(65) Prior Publication Data

US 2005/0247328 A1    Nov. 10, 2005

(51) Int. Cl.
*A61C 15/00* (2006.01)

(52) U.S. Cl. ............... 132/323; 132/326; 132/327

(58) Field of Classification Search ............ 132/322, 132/323, 324, 325, 326, 327
See application file for complete search history.

(56) References Cited

U.S. PATENT DOCUMENTS

| 213,997 | A | * | 4/1879 | Merrill ................. 132/325 |
| 754,841 | A | * | 3/1904 | Bessonet ............... 132/325 |
| 1,105,005 | A | * | 7/1914 | Sonn .................... 132/327 |
| 1,158,890 | A | * | 11/1915 | Bowling ............... 132/325 |
| 1,250,958 | A | * | 12/1917 | Bowling et al. ......... 24/31 B |
| 1,623,231 | A | * | 4/1927 | Bowling et al. ....... 132/324 |
| 2,872,930 | A | * | 2/1959 | Patterson .............. 132/326 |
| 4,564,035 | A | * | 1/1986 | Turner .................. 132/323 |

* cited by examiner

*Primary Examiner*—Todd E. Manahan
(74) *Attorney, Agent, or Firm*—Alan D. Kamrath; Nikolai & Mersereau, P.A.

(57) ABSTRACT

A dental floss holder includes a main body, a retractable member movably mounted on a first end of the main body, a rotation member rotatably mounted in the main body and having a first end engaged with the retractable member to move the retractable member axially relative to the main body by rotation of the rotation member, and a control member rotatably mounted on a second end of the main body and engaged with a second end of the rotation member so as to rotate the rotation member. Thus, the dental floss holder is operated to stretch or release the dental floss easily and conveniently, thereby facilitating the user mounting or replacing the dental floss.

10 Claims, 3 Drawing Sheets

DENTAL FLOSS HOLDER

BACKGROUND OF THE INVENTION

1. Field of the Invention

The present invention relates to a dental floss holder, and more particularly to a dental floss holder that is operated to stretch or release the dental floss easily and conveniently, thereby facilitating the user mounting or replacing the dental floss.

2. Description of the Related Art

A dental floss holder is used to hold and position a dental floss in place, thereby facilitating a user using the dental floss to clean his/her teeth. A conventional dental floss holder in accordance with the prior art reference is disclosed in U.S. Pat. No. 5,503,169 to Won, filed on Aug. 22, 1994, entitled "DENTAL FLOSS HOLDER". In the above-mentioned reference, the locking cap 56 is rotated relative to the body portion 18 to control the spool 54 to stretch or loosen the dental floss 12 so as to adjust the tension of the dental floss 12. However, the locking cap 56 has a smaller rotation portion, so that the user has to exert a larger torque to rotate the locking cap 56, thereby causing inconvenience to the user, especially the older person or the child.

SUMMARY OF THE INVENTION

The primary objective of the present invention is to provide a dental floss holder that is operated to stretch or release the dental floss easily and conveniently, thereby facilitating the user mounting or replacing the dental floss.

Another objective of the present invention is to provide a dental floss holder, wherein the retractable member is movable relative to the main body by rotation of the rotation member to stretch or release the dental floss easily and conveniently, thereby facilitating the user mounting or replacing the dental floss.

A further objective of the present invention is to provide a dental floss holder, wherein the support bars are bent so that they can be deeply extended into the user's mouth, thereby facilitating the dental floss cleaning the user's teeth.

A further objective of the present invention is to provide a dental floss holder, wherein the parts of the dental floss holder are assembled easily and conveniently without aid of an additional tool, thereby facilitating the user mounting the dental floss holder.

A further objective of the present invention is to provide a dental floss holder, wherein the retractable member can be detached from the main body by rotation of the rotation member, thereby facilitating the user clearing the two support bars.

In accordance with the present invention, there is provided a dental floss holder, comprising:

a main body;

a retractable member movably mounted on a first end of the main body;

a rotation member rotatably mounted in the main body and having a first end engaged with the retractable member to move the retractable member axially relative to the main body by rotation of the rotation member; and a control member rotatably mounted on a second end of the main body and engaged with a second end of the rotation member to rotate the rotation member.

Further benefits and advantages of the present invention will become apparent after a careful reading of the detailed description with appropriate reference to the accompanying drawings.

DETAILED DESCRIPTION OF THE INVENTION

Figure 6:
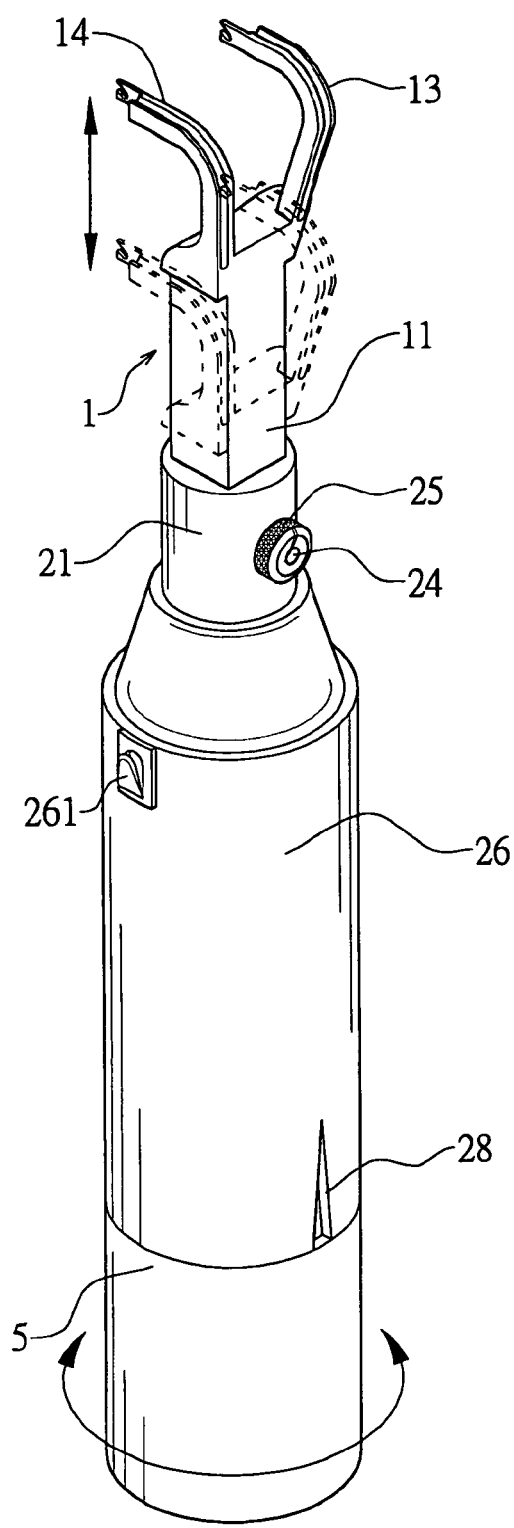
FIG. 6 is a schematic operational view of the dental floss holder as shown in FIG. 1.

Referring to the drawings and initially to FIGS. 1–5, a dental floss holder in accordance with the preferred embodiment of the present invention comprises a main body 2, a retractable member 1 movably mounted on a first end of the main body 2, a rotation member 3 rotatably mounted in the main body 2 and having a first end engaged with the retractable member 1 to move the retractable member 1 axially relative to the main body 2 by rotation of the rotation member 3, and a control member 5 rotatably mounted on a second end of the main body 2 and engaged with a second end of the rotation member 3 to rotate the rotation member 3.

The first end of the main body 2 is formed with a first tube 21 having an inner wall formed with a square hole 22 and an outer wall formed with a threaded portion 24, and a nut 25 is screwed onto the threaded portion 24. The inner wall of the first tube 21 of the main body 2 has an end formed with a plurality of downward extended elastic locking hooks 23. The second end of the main body 2 is formed with a second tube 26 having an inner wall having a first end formed with an annular catch portion 27 located adjacent to the locking hooks 23 and a second end formed with a plurality of axially extended fixing grooves 29 and an outer wall provided with a cutter 261. The second tube 26 of the main body 2 has a distal end formed with a notch 28.

The retractable member 1 has a first end formed with a square bar 11 movably mounted in the square hole 22 of the main body 2. The square bar 11 of the retractable member 1 is formed with a screw bore 12 (see FIG. 4). The retractable member 1 has a second end formed with two substantially inverted L-shaped bent support bars 13 and 14 spaced from each other. Each of the two support bars 13 and 14 has a surface formed with a guide channel 131 and 141 and has a distal end formed with a hooking recess 132 and 142.

The first end of the rotation member 3 is formed with a threaded rod 31 screwed into the screw bore 12 of the square bar 11 and a tapered locking portion 32 located under the threaded rod 31 and locked on the locking hooks 23 of the first tube 21 of the main body 2. The rotation member 3 has a mediate portion formed with a catch ring 33 rested on the catch portion 27 of the second tube 26 of the main body 2. The second end of the rotation member 3 is formed with a hexagonal fixing portion 35 and an outer threaded portion 34 located under the fixing portion 35.

The control member 5 has an inside formed with a hexagonal fixing hole 51 mounted on the fixing portion 35 of the rotation member 3, so that the control member 5 is secured on the second end of the rotation member 3 to rotate the rotation member 3.

The dental floss holder further comprises a cover 6 mounted on the control member 5 and having an inside formed with a screw bore 61 screwed onto the threaded portion 34 of the rotation member 3 to closely position the control member 5 on the second end of the rotation member 3. Preferably, the control member 5 has a bottom formed with a receiving recess 52 for receiving the cover 6.

The dental floss holder further comprises a fixing sleeve 4 mounted in the second tube 26 of the main body 2 and the control member 5 and having a first end rested on the catch ring 33 of the rotation member 3 and a second end rested on the inside of the control member 5. The fixing sleeve 4 has an inner wall formed with a receiving chamber 44 having a closed wall formed with a through hole 43 for passage of the rotation member 3. The fixing sleeve 4 has an outer wall formed with a plurality of axially extended fixing ribs 41 each secured in a respective one of the fixing grooves 29 of the second tube 26 of the main body 2, so that the fixing sleeve 4 is fixed in the second tube 26 of the main body 2 without rotation. The first end of the fixing sleeve 4 is formed with a cutout 42.

Figure 5:
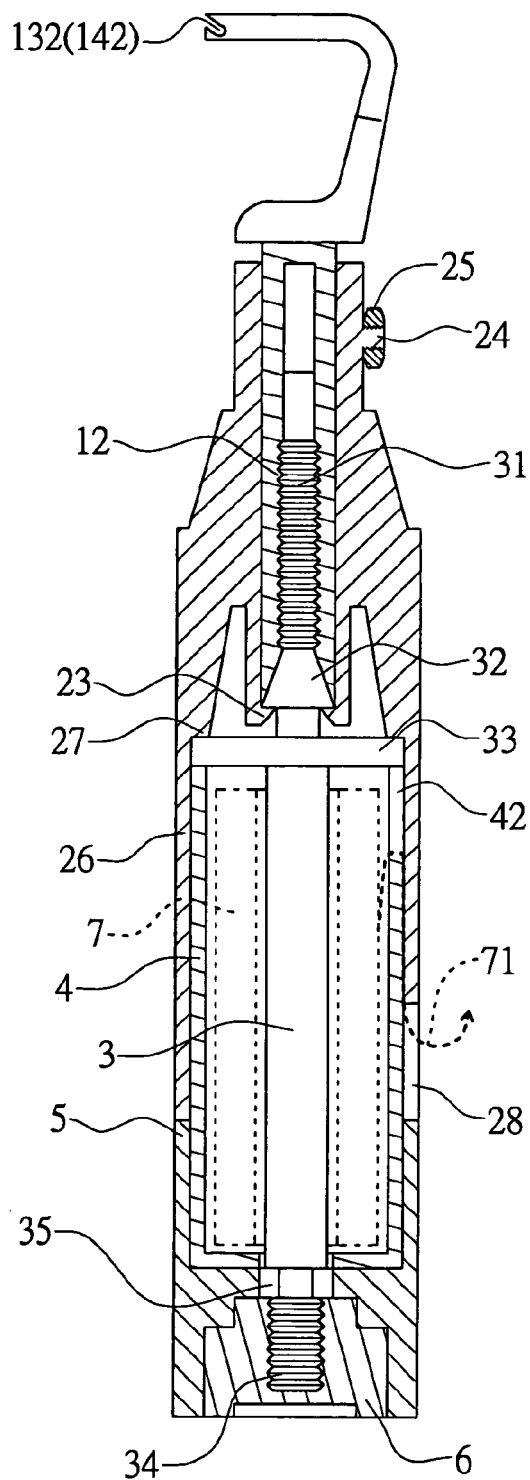
FIG. 5 is a side plan cross-sectional view of the dental floss holder as shown in FIG. 1.

The dental floss holder further comprises a floss spool 7 mounted in the receiving chamber 44 of the fixing sleeve 4 and rotatably mounted on the rotation member 3, and a roll of dental floss 71 wound around the floss spool 7 and having a distal end extended through the cutout 42 of the fixing sleeve 4 and the notch 28 of the second tube 26 of the main body 2 as shown in FIG. 5.

Figure 1:
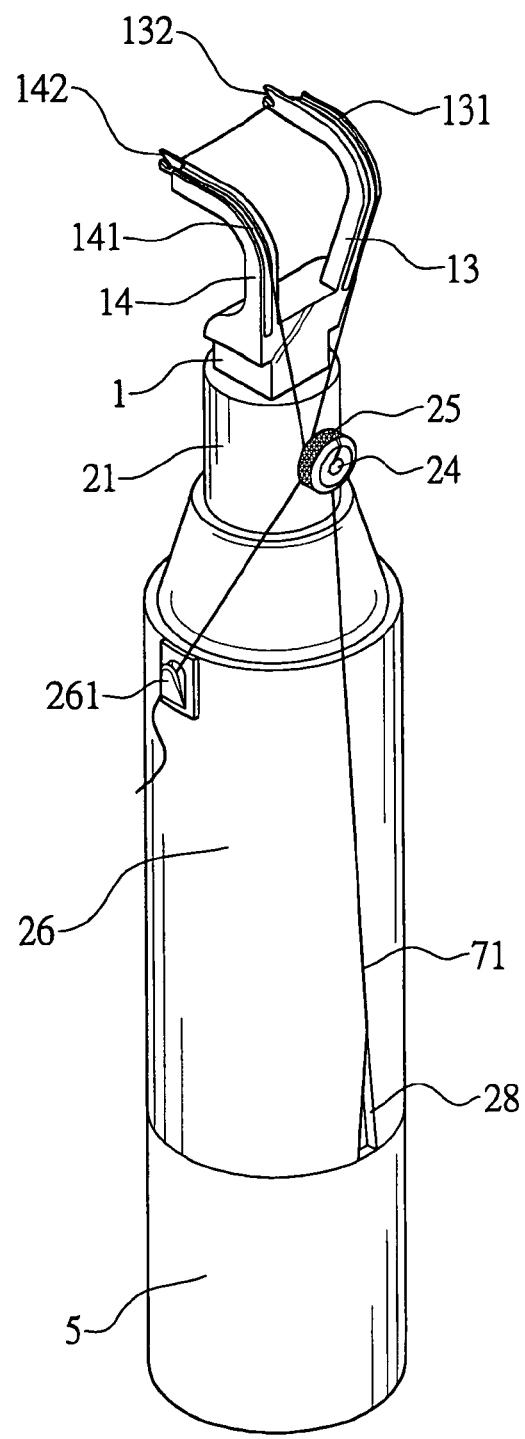
FIG. 1 is a perspective view of a dental floss holder in accordance with the preferred embodiment of the present invention.
Figures 2, 3:
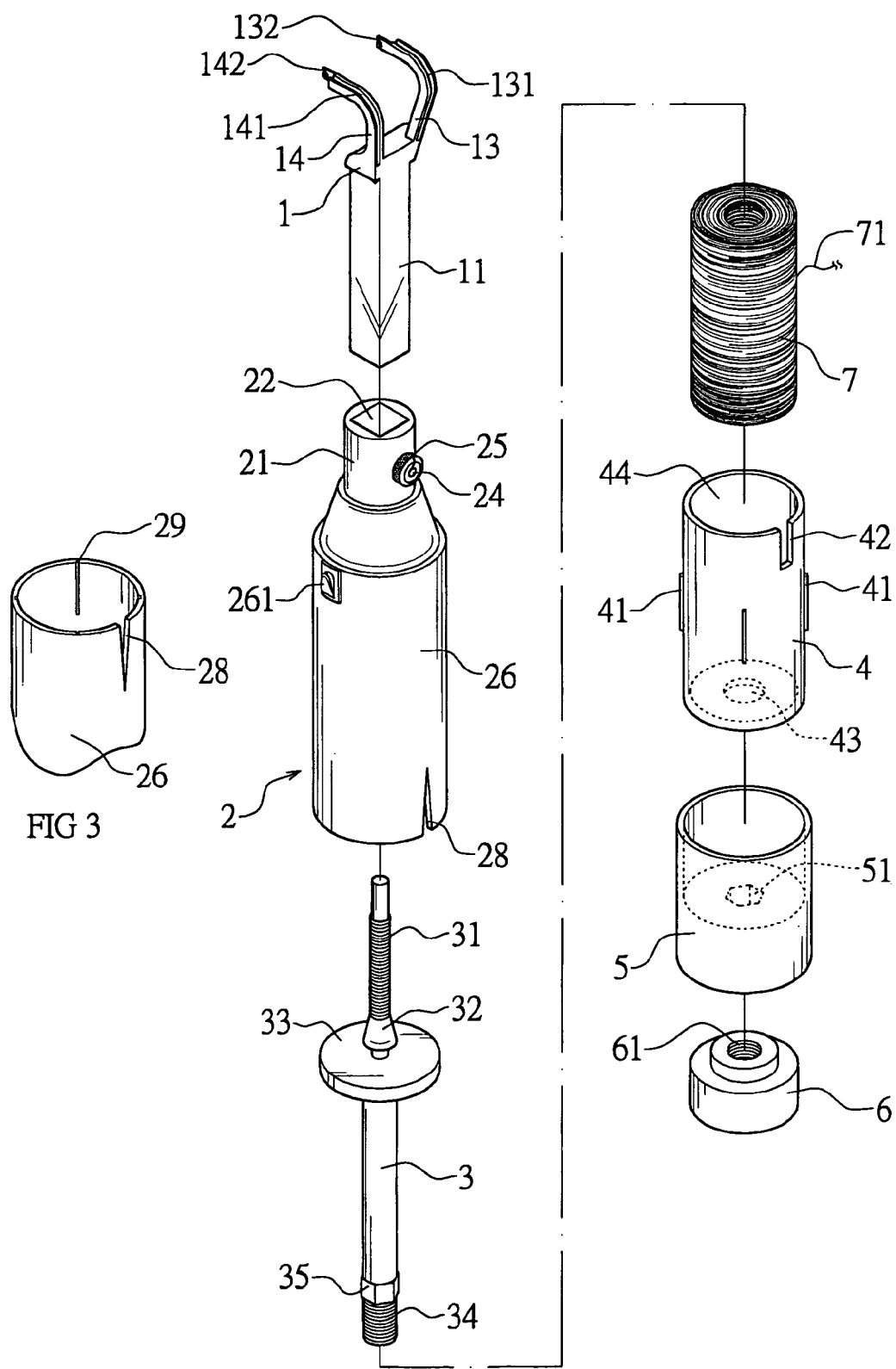
FIG. 2 is an exploded perspective view of the dental floss holder in accordance with the preferred embodiment of the present invention.
FIG. 3 is a perspective view of a main body of the dental floss holder as shown in FIG. 2.
Figure 4:
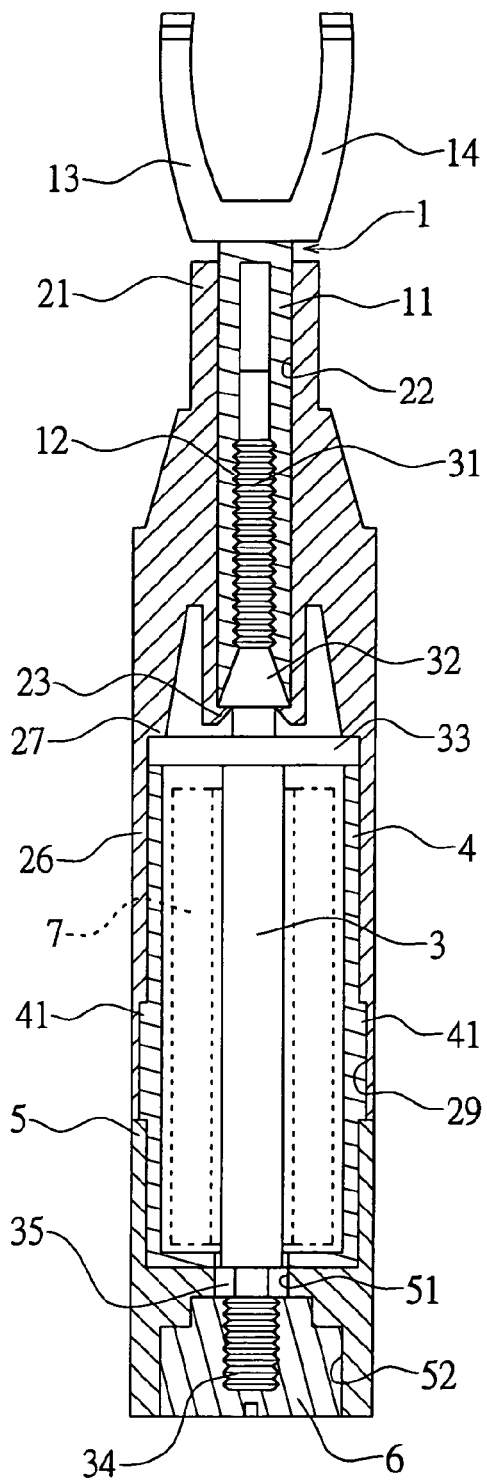
FIG. 4 is a front plan cross-sectional view of the dental floss holder as shown in FIG. 1.

In practice, the distal end of the dental floss 71 is extended through the cutout 42 of the fixing sleeve 4 and is pulled outward from the notch 28 of the second tube 26 of the main body 2 so that the dental floss 71 is pulled outward in a substantially S-shaped manner as shown in FIG. 5 to limit the floss output of the dental floss 71. Then, the distal end of the dental floss 71 is reeved through a gap between the threaded portion 24 and the nut 25 of the main body 2, then extended through the guide channel 131 and the hooking recess 132 of the support bar 13, then extended through the hooking recess 142 and the guide channel 141 of the support bar 14, and is finally reeved through the gap between the threaded portion 24 and the nut 25 of the main body 2, thereby accomplishing the winding work of the dental floss 71 as shown in FIG. 1. The excess part of the dental floss 71 is cut off by means of the cutter 261 mounted on the second tube 26 of the main body 2.

In operation, referring to FIGS. 1–6, the control member 5 is rotated by a user to rotate the rotation member 3 relative to the retractable member 1. At this time, the square bar 11 of the retractable member 1 is limited by the square hole 22 of the main body 2, so that the retractable member 1 is moved in the main body 2 and cannot be rotated relative to the main body 2. In such a manner, when the rotation member 3 is rotated relative to the retractable member 1, the threaded rod 31 of the rotation member 3 is further screwed into the screw bore 12 of the square bar 11 of the retractable member 1 to move the retractable member 1 axially relative to the main body 2, so that the retractable member 1 is movable relative to the main body 2 by rotation of the rotation member 3.

Thus, as shown in FIG. 6, the retractable member 1 is moved to protrude outward from the main body 2 by rotation of the rotation member 3 to provide a tension on the dental floss 71 so as to closely stretch the dental floss 71 for cleaning the user's teeth. After the dental floss 71 is used up, the retractable member 1 is moved to retract into the main body 2 by rotation of the rotation member 3 to release the dental floss 71, thereby facilitating the user replacing the dental floss 71.

Accordingly, the retractable member 1 is movable relative to the main body 2 by rotation of the rotation member 3 so as to stretch or release the dental floss 71 easily and conveniently, thereby facilitating the user mounting or replacing the dental floss 71. In addition, the support bars 13 and 14 are bent so that they can be deeply extended into the user's mouth, thereby facilitating the dental floss 71 cleaning the user's teeth. Further, the parts of the dental floss holder are assembled easily and conveniently without aid of an additional tool, thereby facilitating the user mounting the dental floss holder. Further, the retractable member 1 can be detached from the main body 2 by rotation of the rotation member 3, thereby facilitating the user clearing the two support bars 13 and 14.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A dental floss holder, comprising:
   a main body;
   a retractable member movably mounted on a first end of the main body;
   a rotation member rotatably mounted in the main body and having a first end engaged with the retractable member to move the retractable member axially relative to the main body by rotation of the rotation member; and
   a control member rotatably mounted on a second end of the main body and engaged with a second end of the rotation member to rotate the rotation member;
   wherein the first end of the main body is formed with a first tube having an inner wall formed with a square hole, and the retractable member has a first end formed with a square bar movably mounted in the square hole of the main body;
   the square bar of the retractable member is formed with a screw bore, and the first end of the rotation member is formed with a threaded rod screwed into the screw bore of the square bar;
   the inner wall of the first tube of the main body has an end formed with a plurality of downward extended elastic locking hooks, and the first end of the rotation member is formed with a tapered locking portion located under the threaded rod and locked on the locking hooks of the first tube of the main body.

2. The dental floss holder in accordance with claim 1, wherein the first tube of the main body has an outer wall formed with a threaded portion, and the dental floss holder further comprises a nut screwed onto the threaded portion.

3. The dental floss holder in accordance with claim 1, wherein the retractable member has a second end formed with two substantially inverted L-shaped bent support bars spaced from each other.

4. The dental floss holder in accordance with claim 3, wherein each of the two support bars has a surface formed with a guide channel and has a distal end formed with a hooking recess.

5. The dental floss holder in accordance with claim 1, wherein the second end of the rotation member is formed with a hexagonal fixing portion, and the control member has an inside formed with a hexagonal fixing hole mounted on the fixing portion of the rotation member, so that the control member is secured on the second end of the rotation member to rotate the rotation member.

6. The dental floss holder in accordance with claim 5, wherein the second end of the rotation member is formed with an outer threaded portion located under the fixing portion, and the dental floss holder further comprises a cover mounted on the control member and having an inside formed with a screw bore screwed onto the threaded portion of the rotation member to position the control member on the second end of the rotation member.

7. The dental floss holder in accordance with claim 6, wherein the control member has a bottom formed with a receiving recess for receiving the cover.

8. A dental floss holder, comprising:
a main body;
a retractable member movably mounted on a first end of the main body;
a rotation member rotatably mounted in the main body and having a first end engaged with the retractable member to move the retractable member axially relative to the main body by rotation of the rotation member; and
a control member rotatably mounted on a second end of the main body and engaged with a second end of the rotation member to rotate the rotation member;
wherein the first end of the main body is formed with a first tube having an inner wall formed with a square hole, and the retractable member has a first end formed with a square bar movably mounted in the square hole of the main body;
the second end of the main body is formed with a second tube;
the second tube of the main body has an inner wall having a first end formed with an annular catch portion, and the rotation member has a mediate portion formed with a catch ring rested on the catch portion of the second tube of the main body;
the dental floss holder further comprises a fixing sleeve mounted in the second tube of the main body and the control member and having a first end rested on the catch ring of the rotation member and a second end rested on an inside of the control member;
the inner wall of the second tube of the main body has a second end formed with a plurality of axially extended fixing grooves, and the fixing sleeve has an outer wall formed with a plurality of axially extended fixing ribs each secured in a respective one of the fixing grooves of the second tube of the main body, so that the fixing sleeve is fixed in the second tube of the main body without rotation.

9. The dental floss holder in accordance with claim 8, wherein the second tube of the main body has an outer wall provided with a cutter.

10. A dental floss holder, comprising:
a main body;
a retractable member movably mounted on a first end of the main body;
a rotation member rotatably mounted in the main body and having a first end engaged with the retractable member to move the retractable member axially relative to the main body by rotation of the rotation member; and
a control member rotatably mounted on a second end of the main body and engaged with a second end of the rotation member to rotate the rotation member;
wherein the first end of the main body is formed with a first tube having an inner wall formed with a square hole, and the retractable member has a first end formed with a square bar movably mounted in the square hole of the main body;
the second end of the main body is formed with a second tube;
the second tube of the main body has an inner wall having a first end formed with an annular catch portion, and the rotation member has a mediate portion formed with a catch ring rested on the catch portion of the second tube of the main body;
the dental floss holder further comprises a fixing sleeve mounted in the second tube of the main body and the control member and having a first end rested on the catch ring of the rotation member and a second end rested on an inside of the control member;
the fixing sleeve has an inner wall formed with a receiving chamber having a closed wall formed with a through hole for passage of the rotation member;
the dental floss holder further comprises a floss spool mounted in the receiving chamber of the fixing sleeve and rotatably mounted on the rotation member;
the first end of the fixing sleeve is formed with a cutout, the second tube of the main body has a distal end formed with a notch, and the dental floss holder further comprises a dental floss wound around the floss spool and having a distal end extended through the cutout of the fixing sleeve and the notch of the second tube of the main body.

* * * * *